United States Patent
Park

(10) Patent No.: US 8,870,776 B2
(45) Date of Patent: Oct. 28, 2014

(54) METHOD OF DISPLAYING DIAGNOSTIC IMAGE, IMAGE PROCESSING DEVICE, AND MEDICAL IMAGE SYSTEM FOR PERFORMING THE SAME

(75) Inventor: Moon-ho Park, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 36 days.

(21) Appl. No.: 13/284,403

(22) Filed: Oct. 28, 2011

(65) Prior Publication Data
US 2012/0165673 A1     Jun. 28, 2012

(30) Foreign Application Priority Data

Dec. 24, 2010   (KR) .................. 10-2010-0134908

(51) Int. Cl.
  *A61B 8/14*       (2006.01)
  *A61B 8/00*       (2006.01)
  *A61B 8/08*       (2006.01)

(52) U.S. Cl.
  CPC ............... *A61B 8/0825* (2013.01); *A61B 8/463* (2013.01); *A61B 8/4254* (2013.01); *A61B 8/429* (2013.01)
  USPC ........................................................ 600/443

(58) Field of Classification Search
  USPC ........................................................ 600/443
  See application file for complete search history.

(56) References Cited

U.S. PATENT DOCUMENTS

2007/0239004 A1*  10/2007  Kakee et al. .................. 600/437
2009/0041323 A1*  2/2009  Lachaine et al. .............. 382/131

FOREIGN PATENT DOCUMENTS

| JP | 2008-086742 | 4/2008 |
| JP | 2009-225905 | 10/2009 |
| JP | 2010-166972 | 8/2010 |

OTHER PUBLICATIONS

Chris Rorden. MRIcro manual and tutorial. retrieved Apr. 18, 2013 from <http://www.mccauslandcenter.sc.edu/mricro/mricro/index.html>.*

* cited by examiner

*Primary Examiner* — Long V. Le
*Assistant Examiner* — Colin T Sakamoto
(74) *Attorney, Agent, or Firm* — NSIP Law

(57) ABSTRACT

A method of displaying a diagnostic image is provided. The method includes setting an examination target of a subject, dividing the examination target into a plurality of examination regions, detecting whether a signal region indicated by a signal transmitted from a probe collides with each of the plurality of examination regions, calculating a collision frequency of each of the plurality of examination regions, based on a result of the detecting, and displaying a diagnostic image that indicates a sectional view of the subject and includes information indicating a degree of the collision frequency of each of the plurality of examination regions included in the sectional view, based on the calculation result.

22 Claims, 10 Drawing Sheets

```
for i from 0 to N by 1;
   for j from 0 to M by 1;
      if(Ai Collide with Bj) Increase NumOfCollision[Bj];
   end
end
```

METHOD OF DISPLAYING DIAGNOSTIC IMAGE, IMAGE PROCESSING DEVICE, AND MEDICAL IMAGE SYSTEM FOR PERFORMING THE SAME

CROSS-REFERENCE TO RELATED APPLICATIONS

This application claims the benefit of Korean Patent Application No. 10-2010-0134908, filed on Dec. 24, 2010, in the Korean Intellectual Property Office, the entire disclosure of which is incorporated herein by reference for all purposes.

BACKGROUND

1. Field

The following description relates to a method of displaying a diagnostic image, an image processing device, and a medical image system for performing the same.

2. Description of the Related Art

A medical professional, such as a doctor, examines a subject by using a probe, and determines whether there is a lesion based on an image obtained from the probe. In this case, during manipulation of the probe, the medical professional may inadvertently overlook some examination regions of the subject, or may not perfectly examine some examination regions, which may result in a misdiagnosis.

SUMMARY

According to an aspect, a method of displaying a diagnostic image is provided. The method includes setting an examination target of a subject, dividing the examination target into a plurality of examination regions, detecting whether a signal region indicated by a signal transmitted from a probe collides with each of the plurality of examination regions, calculating a collision frequency of each of the plurality of examination regions, based on a result of the detecting, and displaying a diagnostic image that indicates a sectional view of the subject and includes information indicating a degree of the collision frequency of each of the plurality of examination regions included in the sectional view, based on the calculation result.

The displaying may include displaying a second diagnostic image by changing a first diagnostic image indicating a first sectional view of the subject to the second diagnostic image indicating a second sectional view different from the first sectional view, according to manipulation, and the second diagnostic image may further include information indicating a degree of a collision frequency of each examination region included in the second sectional view of the subject.

The displaying may include displaying the diagnostic image indicating each of sectional views generated from a front surface towards a rear surface of the subject or from the rear surface towards the front surface of the subject, according to manipulation, and the diagnostic image may further include information indicating a degree of a collision frequency of each examination region included in a sectional view indicated by the diagnostic image.

The displaying may include displaying the diagnostic image indicating sectional views generated from a first lateral surface towards a second lateral surface of the subject, according to manipulation, the second lateral surface may be positioned in an imaginary straight line passing through the subject with the first lateral surface, and the diagnostic image may further include information indicating a degree of a collision frequency of each examination region included in a sectional view indicated by the diagnostic image.

The method may further include manipulating a user interface unit implemented as a slider bar so as to display the diagnostic image indicating a sectional view of a desired position of the subject.

The method may further include determining examination regions by setting zero as a collision frequency of examination regions of a non-subject region from among the plurality of examination regions.

The determining of the examination regions may include determining the examination regions by using a switch or pressure sensor included in the probe or by using information indicating whether an image obtained from a signal received from the probe is an empty image.

The setting of the examination target may include setting the examination target by recognizing a plurality of points indicating an outer appearance of the subject by using a sensor included in the probe.

The method may further include providing information indicating that the examination regions of the diagnostic image contains an examination region having a collision frequency that is equal to or less than a threshold value to the user.

A non-transitory computer-readable recording medium may have stored thereon a program for executing the method.

As another aspect, an image processing device is provided. The image processing device includes an examination target setting unit configured to set an examination target of a subject, an examination target dividing unit configured to divide the examination target into a plurality of examination regions, a detector configured to detect whether a signal region indicated by a signal transmitted from a probe collides with each of the plurality of examination regions, a calculator configured to calculate a collision frequency of each of the plurality of examination regions, based on a result of the detecting, and a diagnostic image generating unit configured to generate a diagnostic image that indicates a sectional view of the subject and includes information indicating a degree of the collision frequency of each of the plurality of examination regions included in the sectional view, based on the calculation result.

The diagnostic image generating unit may generate a second diagnostic image by changing a first diagnostic image indicating a first sectional view of the subject to the second diagnostic image indicating a second sectional view different from the first sectional view, according to manipulation, and the second diagnostic image may further include information indicating a degree of a collision frequency of each examination region included in the second sectional view of the subject.

The diagnostic image generating unit may generate the diagnostic image indicating each of sectional views generated from a front surface towards a rear surface of the subject or from the rear surface towards the front surface of the subject, according to manipulation, and the diagnostic image may further include information indicating a degree of a collision frequency of each examination region included in a sectional view indicated by the diagnostic image.

The diagnostic image generating unit may generate the diagnostic image indicating each of sectional views generated from a first lateral surface towards a second lateral surface of the subject, according to manipulation, the second lateral surface may be positioned in an imaginary straight line passing through the subject with the first lateral surface, and the diagnostic image may further include information indicating a degree of a collision frequency of each of examination regions included in a sectional view indicated by the diagnostic image.

The image processing device may further include a user interface unit configured to be manipulated by a user so as to display the diagnostic image indicating a sectional view of a desired position of the subject.

The image processing device may further include an examination region determination unit configured to determine the examination regions by setting zero as a collision frequency of examination regions of a non-subject region from among the plurality of examination regions.

As yet another aspect, a medical image system is provided. The medical image system includes an ultrasonic probe configured to transmitting and/or receiving an ultrasonic signal to and/or from a subject, an image processing device configured to detect whether a signal region indicated by a signal transmitted from the ultrasonic probe collides with each of a plurality of examination regions of the subject, configured to calculate a collision frequency of each of the plurality of examination regions, and configured to generate a diagnostic image that indicates a sectional view of the subject and includes information indicating a degree of the collision frequency of each of the plurality of examination regions included in the sectional view, and a display unit configured to display the diagnostic image.

The image processing device may generate a second diagnostic image by changing a first diagnostic image indicating a first sectional view of the subject to the second diagnostic image indicating a second sectional view different from the first sectional view, according to manipulation, and the second diagnostic image may further include information indicating a degree of a collision frequency of each examination region included in the second sectional view of the subject.

The image processing device may generate the diagnostic image indicating each of sectional views generated from a front surface towards a rear surface of the subject or from the rear surface towards the front surface of the subject, according to manipulation, and the diagnostic image may further include information indicating a degree of a collision frequency of each examination region included in a sectional view indicated by the diagnostic image.

The image processing device may generate the diagnostic image indicating each of sectional views generated from a first lateral surface towards a second lateral surface of the subject, according to manipulation, the second lateral surface may be positioned in an imaginary straight line passing through the subject with the first lateral surface, and the diagnostic image may further include information indicating a degree of a collision frequency of each examination region included in a sectional view indicated by the diagnostic image.

Other features and aspects may be apparent from the following detailed description, the drawings, and the claims.

Figure 1:
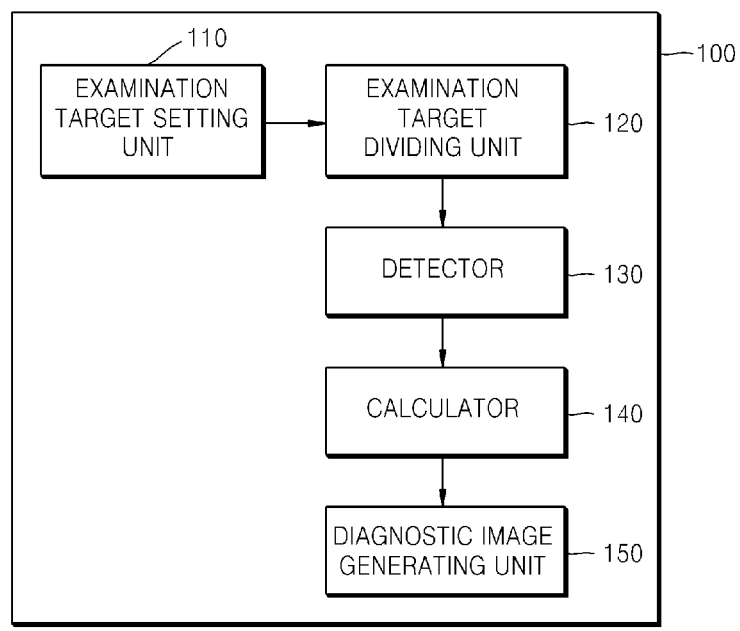
FIG. 1 is a diagram illustrating an example of an image processing device.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

FIG. 1 is a diagram illustrating an example of an image processing device 100. Referring to FIG. 1, the image processing device 100 includes an examination target setting unit 110, an examination target dividing unit 120, a detector 130, a calculator 140, and a diagnostic image generating unit 150.

Elements related to the example are illustrated in FIG. 1. It is understood to those skilled in the art that other general elements may be further included.

The examination target setting unit 110, the examination target dividing unit 120, the detector 130, the calculator 140, the diagnostic image generating unit 150, or any combination thereof of the image processing device 100 may be implemented by a single processor or a plurality of processors. The processor may be implemented by an array of logic gates, or may be implemented with a combination of a general microprocessor and a memory where a program to be run by the microprocessor is stored. It is also understood to those skilled in the art that the processor may be implemented with another form of hardware.

The image processing device 100 performs at least one predetermined operation on data of a subject. In this case, as a non-limiting example, the subject may be a breast, and data about the subject may be an ultrasonic image of the breast.

The examination target setting unit 110 sets an examination target of the subject. In this case, the examination target is a portion of the subject to be examined. For example, the examination target setting unit 110 may set the examination target based on pieces of information about the type, size, and shape of the subject, which are obtained from predetermined information stored in a storage unit (not shown), or as another example, may set the examination target by using a probe (not shown) connected to the image processing device 100.

The examination target dividing unit 120 divides the examination target set by the examination target setting unit 110 into a plurality of examination regions. In this case, as a non-limiting example, the examination target dividing unit 120 may divide the examination target into the plurality of examination regions that are each shaped like a unit hexahedron. Furthermore, the examination target dividing unit 120 may adjust the size of the unit hexahedron so as to adjust the precision to display the examination target.

The detector 130 detects whether a signal region indicated by a signal transmitted from a probe (not shown) collides with each of the examination regions divided by the examination target dividing unit 120. In addition, in response to the probe being moved by manipulation, the detector 130 may detect whether the signal region indicated by the signal transmitted from the probe collides with each of the plurality of examination regions that are set according to the movement of the probe.

As an example, the collision indicates a case where predetermined portions of the signal region and each of the examination regions contact each other for a predetermined period of time. In this case, each of the predetermined portions (for example, 10% or 1% of an entire region) and the predetermined period of time (for example, 1 second or 0.1 seconds) may be set according to a usage environment. As a non-limiting example, in response to 10% or more of the signal region and 10% or more of an examination region contacting each other for 0.1 seconds, the detector 130 may detect that the collision occurs.

The calculator 140 calculates a collision frequency for each of the plurality of examination regions, based on the detection result of the detector 130. For example, the calculator 140 may calculate the collision frequency by adding 1 to the collision frequency whenever a collision occurs. The collision frequency for each of the examination regions may be stored in a storage unit (not shown).

The diagnostic image generating unit 150 generates a diagnostic image that indicates a sectional view of the subject and includes information indicating a degree of the collision frequency of each of the examination regions included in the sectional view of the subject, based on the calculation result of the calculator 140.

The collision frequency may be indicated in a spectrum form, a color spectrum form, or the like. For example, a spectrum color may be changed from a first color to a second color as the collision frequency increases from zero towards a maximum collision frequency that is set. In other words, in response to the maximum collision frequency being 10, the first color is white and the second color is blue, a point where the frequency collision of each of the examination regions is zero may be indicated by white, and a point where the frequency collision of each of the examination regions is about 10 may be indicated by blue. The diagnostic image including information indicating the degree of the collision frequency will be described below with reference to FIG. 2.

In this case, that the signal region indicated by the signal transmitted from the probe collides with an examination region means that examination is performed on the examination region. With reference to an example of a case in response to ultrasonic examination being performed on a breast by using an ultrasonic probe, in response to an ultrasonic signal region indicated by an ultrasonic signal colliding with an examination region once, the ultrasonic examination is performed on the examination region once. In addition, in response to the ultrasonic signal region indicated by an ultrasonic signal colliding with an examination region three times, the ultrasonic examination is performed on the examination region three times. Thus, in response to there being an examination region that does not collide with the ultrasonic signal region, the ultrasonic examination is not performed on the examination region, which may result in a misdiagnosis.

Thus, a user may recognize a region of the subject on which examination is not performed at all, or a region of the subject on which a small number of examinations are performed, and thus, the subject may be correctly diagnosed.

Figure 2:
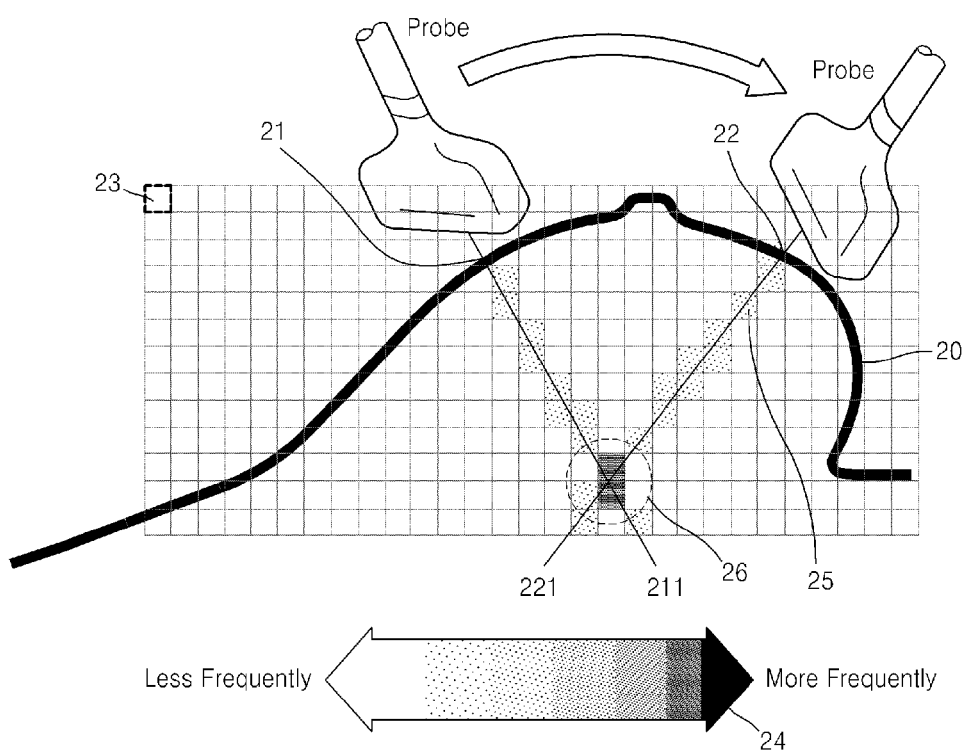
FIG. 2 is a diagram illustrating an example of a method of displaying a degree of a collision frequency.

FIG. 2 is a diagram illustrating an example of a method of displaying a degree of a collision frequency. Referring to FIGS. 1 and 2, FIG. 2 shows signal regions 211 and 221 indicated by signals transmitted from the probe in response to a probe being moved on a subject 20 from a first point 21 to a second point 22.

A diagnostic image shown in FIG. 2 further includes information indicating the degree of the collision frequency of a single examination region 23 that is divided from a set examination target. As indicated by an arrow 24, colors of a plurality of examination regions may be determined according to the degree of the collision frequency.

Thus, the diagnostic image generating unit 150 may generate the diagnostic image in which a color of a first region 25 colliding with the signal regions 211 and 221 once is different from a color of a second region 26 colliding with the signal regions 211 and 221 twice. Thus, the user may determine whether the examination region is examined with reference to the diagnostic image, and thus, may correctly diagnose the subject.

The above-described method using the color spectrum is a non-limiting example. In other words, it is understood that other implementations may be within the scope of the teachings herein, for example, a method of indicating the collision frequency for each of the examination regions by Arabic numerals, or a method of changing a color of an examination region colliding with a signal region a predetermined time or more may be used.

Figure 3:
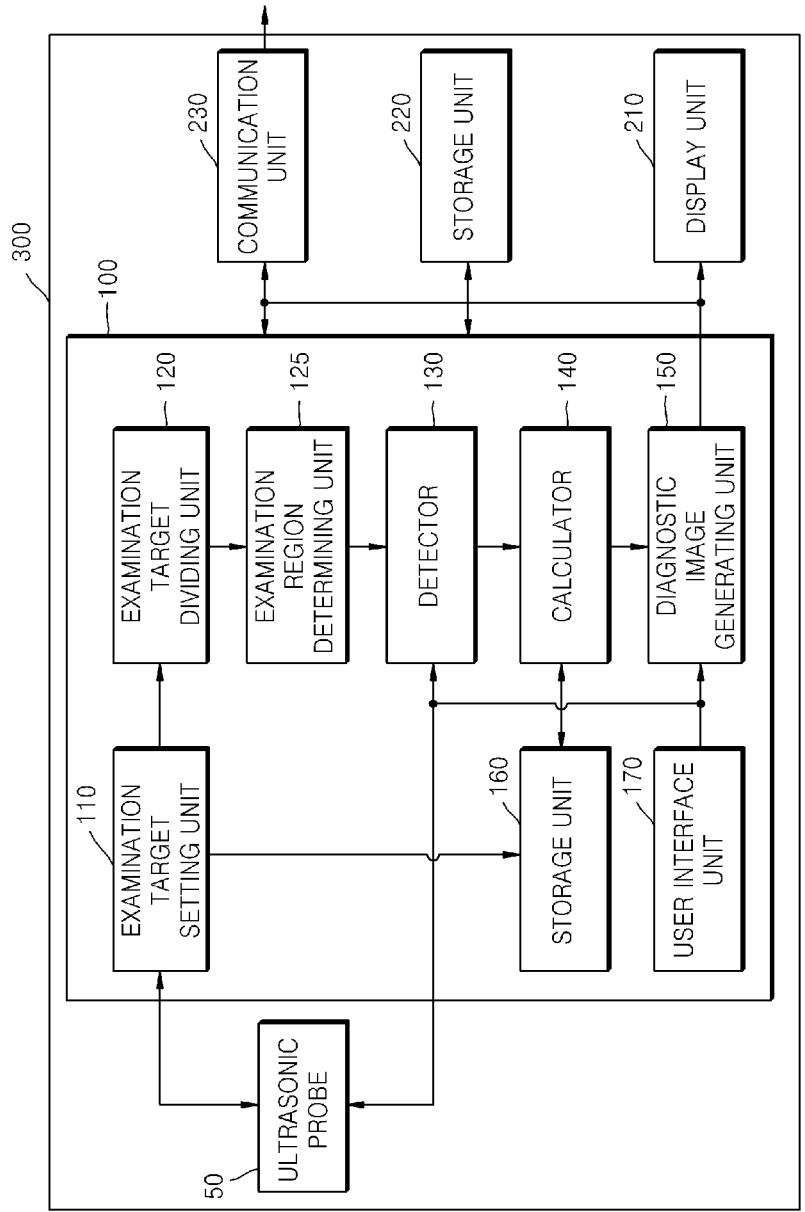
FIG. 3 is a diagram illustrating an example of a medical image system.

FIG. 3 is a diagram illustrating an example of a medical image system 300. Referring to FIG. 3, the medical image system 300 includes an ultrasonic probe 50, the image processing device 100, a display unit 210, a storage unit 220, and a communication unit 230. The image processing device 100 includes the examination target setting unit 110, the examination target dividing unit 120, an examination region determining unit 125, the detector 130, the calculator 140, the diagnostic image generating unit 150, a storage unit 160, and a user interface unit 170.

Elements related to the example illustrated in FIG. 3. It is understood to those skilled in the art that other general elements may be further included.

The image processing device 100 illustrated in FIG. 3 is an example of the image processing device 100 of FIG. 1. Thus, the image processing device 100 is not limited to the elements illustrated in FIG. 3. The description described with reference to FIG. 1 also applies to the medical image system 300 of FIG. 3, and thus, is not repeated for conciseness.

The image processing device 100 detects whether a signal region indicated by a signal transmitted from the ultrasonic probe 50 collides with each of a plurality of examination regions of a subject, calculates a collision frequency for each of the examination regions, and generates a diagnostic image that indicates a sectional view of the subject and includes information indicating a degree of the collision frequency of each of the examination regions included in the sectional view of the subject. In this case, as a non-limiting example, the subject may be a breast and the diagnostic image may be an ultrasonic image of the breast obtained by using the ultrasonic probe 50.

The ultrasonic probe 50 transmits and/or receives an ultrasonic signal to and/or from the subject. That is, the ultrasonic probe 50 transmits and/or receives the ultrasonic signal to and/or from an examination portion of the subject.

The ultrasonic probe 50 may include a transducer that converts an electrical signal into an ultrasonic signal and converts an ultrasonic signal reflected off the subject into an electrical signal, and may include a beam former that forms a plurality of transmission signals transmitted from the ultrasonic probe 50 in consideration of a time delay due to a distance difference.

The ultrasonic probe 50 may include a sensor for obtaining position information. In this case, the position information may include information about a direction of the ultrasonic probe 50. Thus, the image processing device 100 may set the examination target of the subject or may detect whether the signal transmitted from the ultrasonic probe 50 collides with each of the examination regions, by using the sensor included in the ultrasonic probe 50, as will be described below.

In addition, the signal region indicated by the signal transmitted from the ultrasonic probe 50 may be formed according to the type of the ultrasonic probe 50. For example, in response to the ultrasonic probe 50 being a linear probe, the signal region may be formed to have a square shape. As another example, in response to the ultrasonic probe 50 being a convex probe, the signal region may be formed to have a trapezoidal shape.

In this case, the signal region may be divided into a plurality of regions (for example, regions with a square shape) and may be expressed in a combination of relative positions based on a predetermined reference point. In addition, the movement of the ultrasonic probe 50 may be expressed by the movement of the reference point, such as translation and rotation. The signal region indicated by the signal transmitted from the ultrasonic probe 50 is described below with reference to FIG. 4.

The image processing device 100 performs at least one predetermined operation on the ultrasonic image of the subject, obtained by using the ultrasonic probe 50, so as to generate the diagnostic image.

The examination target setting unit 110 sets the examination target of the subject. For example, the examination target setting unit 110 may set the examination target based on pieces of information about the type, size, shape, or any combination thereof of the subject, which are obtained from predetermined information stored in the storage unit 160. In other words, in response to the subject being a breast, the examination target setting unit 110 may set the examination target of the subject by using the information stored in the storage unit 160.

As another example, the examination target may be set by using the ultrasonic probe 50 connected to the image processing device 100. As an example, the examination target of the subject may be set by using the sensor included in the ultrasonic probe 50.

In other words, the examination target setting unit 110 may recognize a plurality of points indicating an outer appearance of the subject so as to set the examination target by using the sensor included in the ultrasonic probe 50. In this case, the points indicating the outer appearance of the subject may refer to points indicating a circumscribed shape of the subject.

The ultrasonic probe 50 may recognize each of the points indicating the outer appearance of the subject by manipulation of the user. In this case, as a non-limiting example, the user may be a medical expert who uses the image processing device 100 or the medical image system 300, such as a doctor, a nurse, or a medical image expert.

A method of setting the examination target by using the ultrasonic probe 50 will be described with reference to FIG. 5.

The examination target dividing unit 120 divides the examination target set by the examination target setting unit 110 into a plurality of examination regions. The examination region determining unit 125 determines the examination regions by setting zero as a collision frequency of regions (hereinafter, referred to as 'examination regions of non-subject region') that are not located in a subject region from among the divided examination regions. In other words, the examination region determining unit 125 may determine regions having a collision frequency that is not zero as the examination regions.

In this case, a method of determining the examination regions of a non-subject region from among the examination regions divided by the examination region determining unit 125 may be embodied with a form of hardware or software.

In response to the method being implemented as hardware, the examination region determining unit 125 may set the examination regions by using a switch or pressure sensor included in the ultrasonic probe 50.

For example, the examination region determining unit 125 may use the switch or pressure sensor included in the ultrasonic probe 50. As an example, in response to a probe 50 contacting the subject, as the user turns-on the switch included in the probe 50, the examination region determining unit 125 may determine regions where the switch included in the probe 50 is turned-off as the examination regions of non-subject region.

As another example, in response to the probe 50 contacting the subject, as the pressure sensor included in the probe 50 recognizes that the probe 50 contacts the subject, the examination region determining unit 125 may determine regions that are not recognized by the pressure sensor included in the probe 50 as the examination regions of non-subject region.

In response to the method being implemented as software, the examination region determining unit 125 may determine the examination regions by using whether an image obtained from a signal received from the ultrasonic probe 50 is an empty image.

For example, the examination region determining unit 125 may determine regions where an image obtained from the signal received from the ultrasonic probe 50 is an empty image as the examination regions of the non-subject region. In this case, the empty image refers to a case where there is almost no image in the image obtained from the signal received from the ultrasonic probe 50. As a non-limiting example, the case where there is almost no image refers to a case where a predetermined image occupies less than 1% of an area of the image obtained from the signal received from the ultrasonic probe 50.

Thus, the examination regions of the non-subject region may be excluded from among the examination regions by using the examination region determining unit 125, thereby improving reliability of the examination.

The examination target is divided into examination regions, and the divided examination regions are divided into the examination region of the subject region and the examination regions of the non-subject region, which will be described with reference to FIG. 6.

The detector 130 detects whether a signal region indicated by an ultrasonic signal transmitted from the ultrasonic probe 50 collides with each of the divided examination region. The calculator 140 calculates a collision frequency of each of the examination regions, based on the detection result of the detector 130. A method of detecting whether the signal region collides with each of the examination regions and calculating the collision frequency will be described with reference to FIG. 7.

The diagnostic image generating unit 150 generates a diagnostic image that indicates sectional view of the subject and includes information indicating a degree of the collision frequency of each of the examination regions included in the sectional view of the subject, based on the calculation result of the calculator 140.

The diagnostic image generating unit 150 may generate a second diagnostic image by changing a first diagnostic image indicating a first sectional view of the subject to the second diagnostic image indicating a second sectional view of the subject, according to manipulation. In this case, the second diagnostic image may further include information indicating a degree of collision frequency of each of the examination regions included in the second sectional view.

For example, the user may change the first diagnostic image indicating the first sectional view of the subject to the second diagnostic image indicating the second sectional view different from the first sectional view by manipulating the user interface unit 170. In this case, the user interface unit 170 may be embodied in the form of a slider bar. Thus, the user may view the information indicating the degree of the collision frequency of various regions of the subject by manipulating the user interface unit 170, thereby improving the reliability of the examination.

As another example, the diagnostic image generating unit 150 may generate diagnostic image indicating each of sectional views generated from a front surface towards a rear surface of the subject, or from the rear surface towards the front surface of the subject, according to manipulation. In this case, the diagnostic images generated by the diagnostic image generating unit 150 further include information indicating the degree of the collision frequency of each of the examination regions included in the sectional view of the diagnostic image. Thus, the diagnostic image generating unit 150 may generate a diagnostic image indicating a sectional view spaced apart from the front surface or the rear surface of the subject by a predetermined distance. In this case, the predetermined distance may be changed by manipulation.

The user may view the diagnostic image of each of the sectional views generated from the front surface towards the rear surface of the subject or from the rear surface towards the front surface of the subject by manipulating the user interface unit 170. The user interface unit 170 may be implemented as a slider bar, and the user may view a sectional view of a desired position of the subject by manipulating the slider bar, which will be described with reference to FIG. 8.

As another example, the diagnostic image generating unit 150 may generate diagnostic image indicating each of sectional views generated from a first lateral surface towards a second lateral surface of the subject according to manipulation. In this case, the second lateral surface is positioned in an imaginary straight line passing through the subject with the first lateral surface, and the diagnostic images generated by the diagnostic image generating unit 150 further include information indicating the degree of the collision frequency of each of the examination regions included in the sectional view of the diagnostic image. Thus, the diagnostic image generating unit 150 may generate a diagnostic image indicating a sectional view apart from the first lateral surface or the second lateral surface of the subject by a predetermined distance. In this case, the predetermined distance may be changed by manipulation.

The user may view the diagnostic image of each of the sectional views generated from the first lateral surface towards the second lateral surface of the subject by manipulating the user interface unit 170. The user interface unit 170 may be implemented as a slider bar and the user may view a sectional view of a desired position of the subject by manipulating the slider bar, which will be described with reference to FIG. 9.

Thus, the diagnostic image generating unit 150 may generate a diagnostic image indicating a sectional view apart from the front surface or the rear surface of the subject, the first lateral surface or the second lateral surface by a predetermined distance, or a combination thereof. In this case, the predetermined distance may be changed by manipulation. Thus, the user may view whether the examination is performed on a desired position of the subject and may view an examination value, thereby improving results of the examination.

The storage unit 160 stores data generated during operations of the image processing device 100. For example, the storage unit 160 may store information about the type, size, shape, or any combination thereof of the subject. The type of subject may be breasts, the abdomen, the liver, veins, the womb, prostate, the testis, the musculoskeletal system, the thyroid, or the like. The size and shape of the subject may be information about the size and shape corresponding to the type of subject. As another example, in response to the subject being the breast, the storage unit 160 may store information about the size and shape of the breast.

In addition, the storage unit 160 may store the collision frequency of each of the examination regions. In other words, in response to the storage unit 160 storing the collision frequency of each of the examination regions, the stored collision frequency may be updated by the calculator 140.

The storage unit 160 may correspond with a storage medium. The storage unit 160 may include a Hard Disk Drive (HDD), Read Only Memory (ROM), Random Access Memory (RAM), flash memory, a memory card, or the like.

The user interface unit 170 receives input information from the user and outputs information to the user. For example, the user interface unit 170 includes input/output devices included in the image processing device 100, such as a display panel, a mouse, a key board, input buttons, a touch screen, a liquid crystal display (LCD) screen, a monitor, a speaker, and the like.

Thus, the user may manipulate the user interface unit 170 so as to display the diagnostic image indicating the sectional view of a desired position of the subject. In this case, the user interface unit 170 may be implemented as a slider bar, as will be described with reference to FIGS. 8 and 9.

In addition, the user interface unit 170 provides information indicating that the examination regions of the diagnostic image generated by the diagnostic image generating unit 150 contains an examination region having a collision frequency that is equal to or less than a threshold value. In this case, the threshold value may be, as a non-limiting example, 2 times. It is understood as being within the scope of the teachings herein that the threshold value may be other than 2 times. The user interface unit 170 may provide the information to the user by using various methods such as a buzzer sound, a warning sound, a warning message, emission of a light-emitting device, flickering of a light-emitting device, or the like.

Thus, the image processing device 100 may notify the user about information indicating that the diagnostic image contains an examination region that is not sufficiently examined, thereby improving results of the examination.

The user interface unit 170 may display the diagnostic image generated by the diagnostic image generating unit 150. As another aspect, the display unit 210 for displaying the diagnostic image may be disposed outside the image processing device 100, rather than being disposed in the image processing device 100.

The display unit 210 displays the diagnosis image generated by the image processing device 100. As an example, the display unit 210 in the medical image system 300 includes output devices, such as a display panel, a touch screen, and a monitor, and a software module for operating the output devices.

The storage unit 220 stores the diagnosis image generated by the image processing device 100. As an example, the storage unit 220 may correspond to a storage medium. It is understood that the storage unit 220 may include a Hard Disk Drive (HDD), Read Only Memory (ROM), Random Access Memory (RAM), flash memory, a memory card, or the like.

The communication unit 230 transmits the diagnosis image generated by the image processing device 100 to an external device and receives data from the external device. Herein, the external device may be another medical image system at another place, a computer system, a fax machine, or the like.

The communication unit 230 may transmit and/or receive data to and/or from the external device through a wired or wireless network. Herein, as a non-limiting example, the network includes the Internet, a Local Area Network (LAN), a Wireless LAN, a Wide Area Network (WAN), a Personal Area Network (PAN), and the like; as another aspect, it is understood as being within the scope of the teachings herein that the network may be other kinds of networks for transmitting and receiving information.

According to another aspect, the storage unit 220 and the communication unit 230 may further include image interpretation and search functions to be integrated to one body, such as a Picture Archiving Communication System (PACS).

Therefore, the medical image system 300 may display the clear diagnosis image to determine whether the entire regions of the subject are examined, and store and transmit the image. Accordingly, examinees and medical professionals may obtain more correct diagnosis information.

Figure 4:
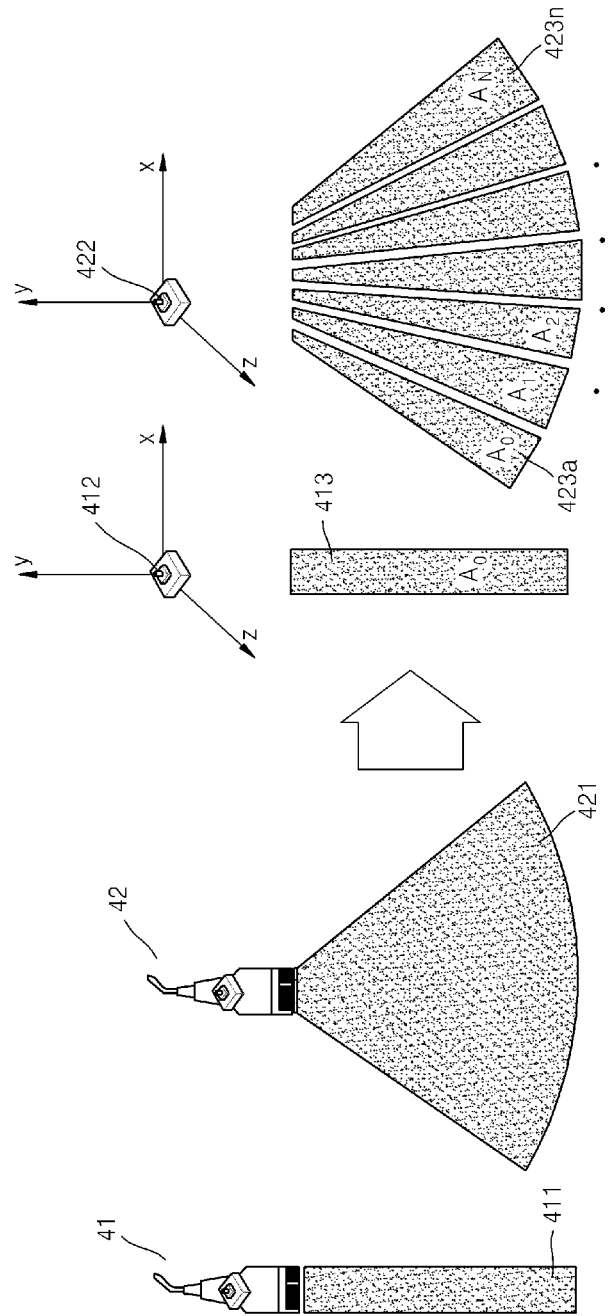
FIG. 4 is a diagram illustrating an example of a signal region indicated by a signal transmitted from an ultrasonic probe.

FIG. 4 is a diagram illustrating an example of the signal region indicated by the signal transmitted from the ultrasonic probe 50 of FIG. 3. Referring to FIGS. 3 and 4, a linear probe 41 and a convex probe 42 illustrate examples of the ultrasonic probe 50. Referring to FIG. 4, the linear probe 41 forms a signal region 411 having a rectangular shape, and the convex probe 42 forms a signal region 421 having a trapezoidal shape.

A signal region may be expressed in a combination of relative positions based on a predetermined reference point, or as another example, may be divided into a plurality of regions and may be expressed in a combination of relative positions based on a predetermined reference point.

For example, the signal region 411 indicated by the signal transmitted from the linear probe 41 may be expressed in a combination of relative positions based on a reference point 412, and the signal region 421 indicated by the signal transmitted from the convex probe 42 may be divided into a plurality of regions 423a through 423n and then may be expressed in a combination of relative positions based on a reference point 422.

The case of the convex probe 42 is now described. 'A' indicating the signal region 421 may be represented according to Equation 1.

$$A = \sum_{i=0}^{N} A_i, A_i = \{a_{i1}, a_{i2}, a_{i3}, a_{i4}\} \quad (1)$$

In Equation 1, A denotes the signal region 421, $A_i$ denotes the regions 423a through 423n divided from the signal region 421, and $a_{i1}$, $a_{i2}$, $a_{i3}$, and $a_{i4}$ denote coordinates of first, second, third, and fourth vertexes of $A_i$ based on the reference point 422, respectively.

Thus, the signal region may be divided into a plurality of regions and then may be expressed as a combination of relative positions based on a predetermined reference point.

In response to the ultrasonic probe 50 being moved, the movement of the ultrasonic probe 50 may be expressed by the movement of the reference point, such as translation and rotation. Thus, in response to the ultrasonic probe 50 being moved, a signal region A' indicated by a signal transmitted from the ultrasonic probe 50 may be represented according to Equation 2.

$$A' = M^p \cdot A \quad (2)$$

In Equation 2, A corresponds to a signal region prior to the movement of the ultrasonic probe 50, A' corresponds to a signal region after the movement of the ultrasonic probe 50, and $M^p$ corresponds to a transformation matrix to which translation and rotation of the ultrasonic probe 50 are reflected.

As described above, the signal region indicated by the signal transmitted from the ultrasonic probe 50 and the signal region in response to the ultrasonic probe 50 being moved may each be expressed. In addition, the detector 130 may correctly detect whether the signal region collides with each of the examination regions, based on the above signal regions.

Figure 5:
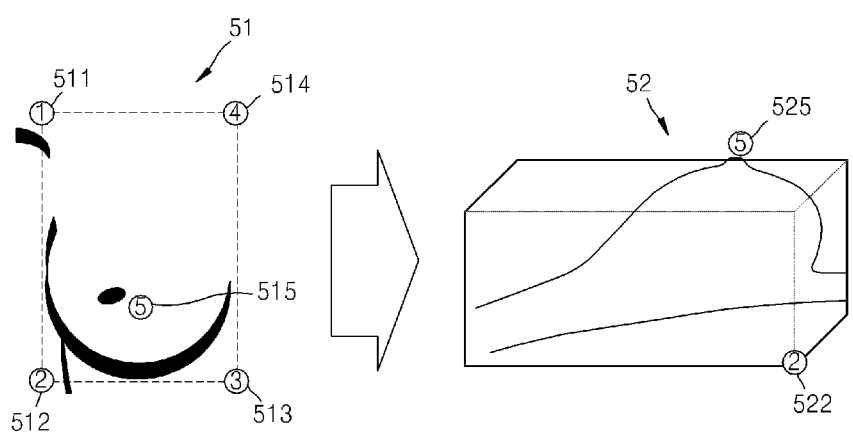
FIG. 5 is a diagram illustrating an example of a method of setting an examination target by using the ultrasonic probe.

FIG. 5 is a diagram illustrating an example of a method of setting an examination target by using the ultrasonic probe 50. Referring to FIG. 5, drawing 51 indicates a plurality of points indicating an outer appearance of the subject, and drawing 52 indicates that the examination target is set.

In the drawing 51 indicating the points indicating the outer appearance of the subject, first through fifth points 511 through 515 indicating the outer appearance of the subject are indicated. In this case, the second point 512 may corresponds to the lowermost position, and the fifth point 515 may corresponds to the uppermost position for providing height information.

With reference to FIGS. 3 and 5, the user may manipulate the ultrasonic probe 50 so that the ultrasonic probe 50 may recognize the first through fifth points 511 through 515, and thus, the examination target setting unit 110 may receive data from the ultrasonic probe 50 so as to set the examination target.

With reference to the drawing 52 in which the examination target is set, the examination target may be set to be a box type which circumscribes the subject based on a second point 522, which corresponds to the lowermost position, and a fifth point 525, which corresponds to the uppermost position.

As another aspect, the box type circumscribing the subject is an example of a method of setting the examination target, and thus it is understood as being within the scope of the teachings herein that other implementations of the method of setting the examination target may be used.

Figure 6:
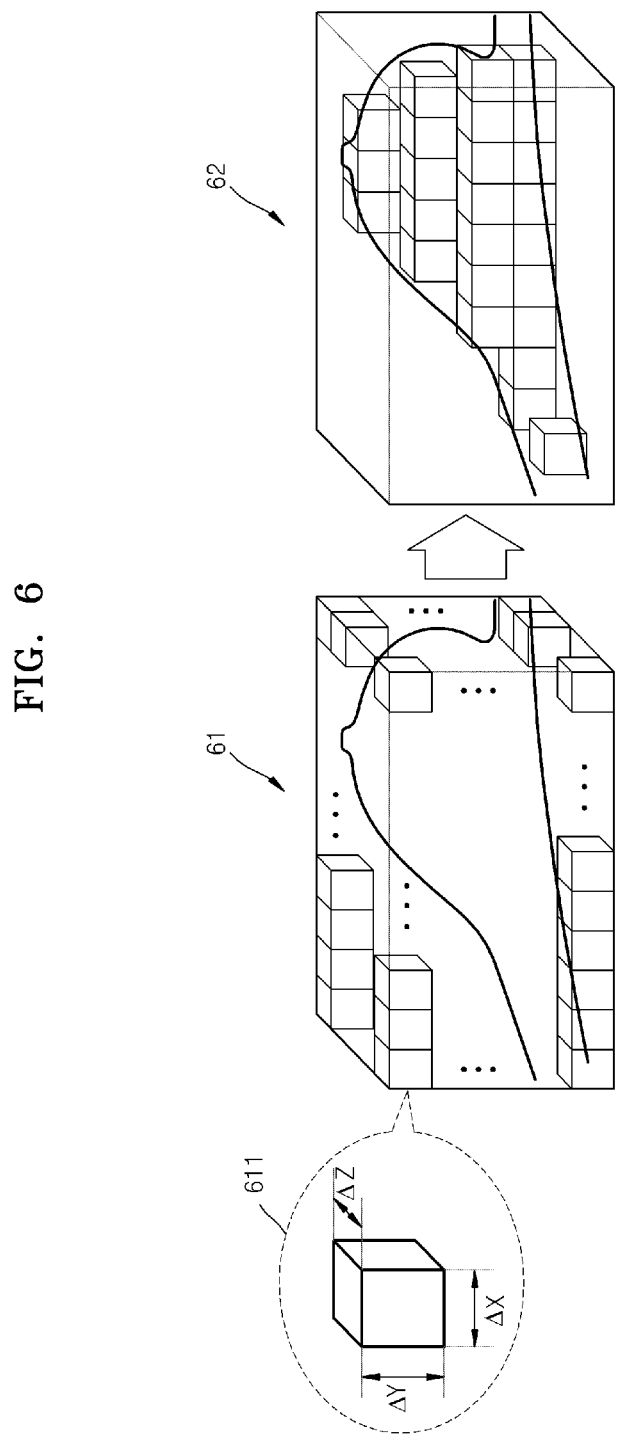
FIG. 6 is a diagram illustrating an example of a method of determining examination regions.

FIG. 6 is a diagram illustrating an example of a method of determining examination regions. Referring to FIGS. 3 and 6, the examination target is set by the examination target setting unit 110. In addition, in drawing 61, the examination target is divided into examination regions by the examination target dividing unit 120. In drawing 62, the examination regions are determined.

With reference to the drawing 61 in which the examination target is divided into examination regions, the examination target dividing unit 120 may divide the examination target set by the examination target setting unit 110 into the examination regions that are each shaped like a unit hexahedron. In this case, a size 611 of the unit hexahedron may be represented by using delta x, delta y and delta z. Thus, the user may adjust the size and number of examination regions by adjusting the size of the unit hexahedron, and thus, the user may adjust the precision of the diagnostic image generated by the image processing device 100.

In addition, the examination region determining unit 125 determines the examination regions by setting zero as a collision frequency of the examination regions of the non-subject region. Thus, the examination region determining unit 125 may determine regions having a collision frequency that is not zero as the examination regions, which is shown in the drawing 62 in which the examination region is determined.

Thus, the image processing device 100 may determine the examination regions of the subject region from among the examination regions, thereby improving the results of the examination.

Figure 7:
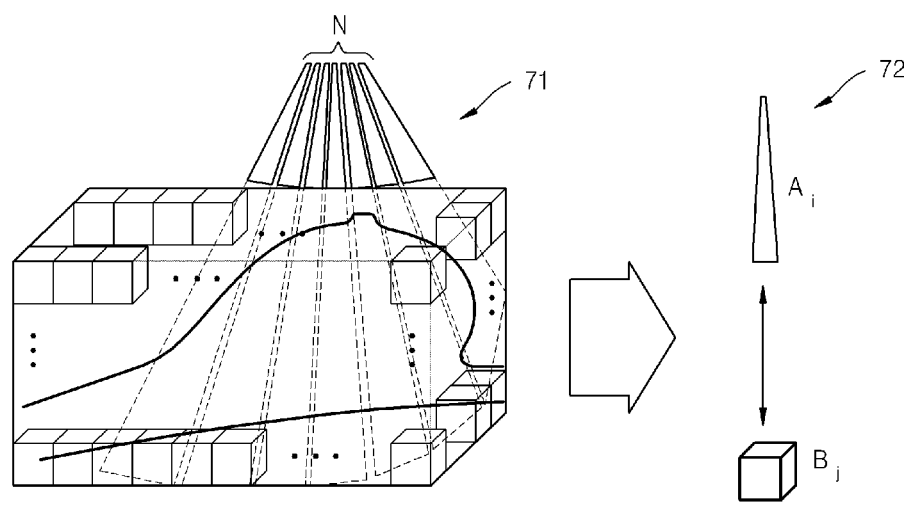
FIG. 7 is a diagram illustrating an example of a method of detecting whether a signal region collides with each of examination regions and calculating a collision frequency.

FIG. 7 is a diagram illustrating an example of a method of detecting whether the signal region collides with each of the examination regions and calculating the collision frequency. Referring to FIGS. 3 and 7, in response to the detector 130 detecting whether the signal region collides with each of the examination regions, the signal region and each of the examination regions are divided into N regions and M regions, respectively.

In drawing 71, in response to a signal region indicated by a signal transmitted from the ultrasonic probe 50 being divided into N signal regions, the N signal regions contact the examination target. In drawing 72, one signal region $A_i$ from among a plurality of signal regions collides with any one examination region $B_j$ from among a plurality of examination regions. As illustrated in the drawing 72, in response to predetermined portions (for example, 5% or more of an entire region) of the signal region $A_i$ and the examination region $B_j$ contacting each other, the detector 130 detects that the signal region $A_i$ collides with the examination region $B_j$.

Code 73 corresponds to a software program code indicating a method of detecting (if (Ai collides with Bj)) whether the signal region $A_i$ from among a plurality of signal regions collides with the examination region $B_j$ from among a plurality of examination regions and calculating a collision frequency, as a collision frequency, (Increase NumOfCollision [Bj]) is increased by, for example, 1, based on the detection result. Thus, the detector 130 may detect whether the signal region indicated by the ultrasonic signal transmitted from the ultrasonic probe 50 collides with each of the examination regions. The calculator 140 may calculate the collision frequency of each of the examination regions based on the detection result of the detector 130. Further description of the code is omitted for conciseness as programmers skilled in the art can construe the code as described herein.

Figure 8:
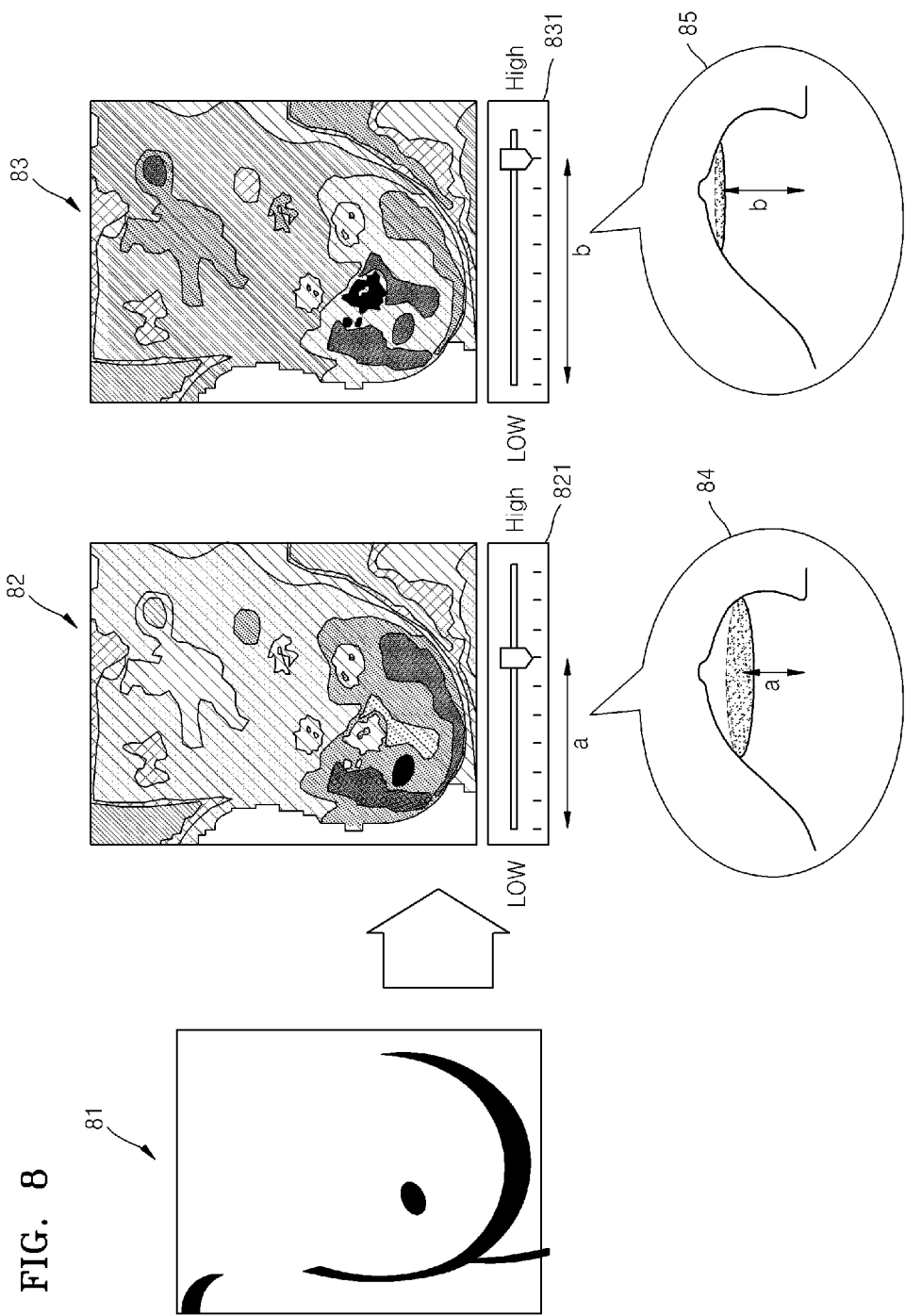
FIG. 8 is a diagram illustrating an example of a method of viewing diagnostic image indicating each of sectional views generated from a front surface towards a rear surface of a subject or from the rear surface towards the front surface of the subject.

FIG. 8 is a diagram illustrating an example of a method of viewing diagnostic image indicating each of sectional views generated from a front surface towards a rear surface of the subject or from the rear surface towards the front surface of the subject. Referring to FIGS. 3 and 8, drawing 81 illustrates the front surface of the subject, first diagnostic image 82 illustrates a first sectional view of the subject, and second diagnostic image 83 illustrates a second sectional view of the subject. In this case, the first diagnostic image 82 and the second diagnostic image 83 further include information corresponding to a degree of a collision frequency of each of the examination regions included in the first sectional view and the second sectional view, respectively. The degree of the collision frequency of each of the first diagnostic image 82 and the second diagnostic image 83 is illustrated as a spectrum.

The user may view the diagnostic images for each respective sectional view generated from the front surface towards the rear surface of the subject by manipulating the user interface unit 170. In this case, the user interface unit 170 may be implemented as slider bars 821 and 831.

As a non-limiting example, in response to the subject being a breast, the front surface of the subject corresponds to a front surface of a human body, that is, a portion around the nipple, and the rear surface of the subject corresponds to a rear surface of the human body, that is a portion around the back.

For example, in response to the slider bar 821 being manipulated by the user, the first sectional view indicated by the first diagnostic image 82 indicates a first sectional view generated so as to be spaced apart from the rear surface of the subject by a distance 'a', as shown in drawing 84.

In addition, in response to the slider bar 831 being manipulated by the user, the second sectional view indicated by the second diagnostic image 83 indicates a second sectional view generated so as to be spaced apart from the rear surface of the subject by a distance 'b', as shown in drawing 85.

Similarly, the user may view diagnostic images indicating sectional views in desired positions by manipulating the user interface unit 170 implemented as the slider bar 821 and 831. In this case, the diagnostic image further includes the information indicating the degree of the collision frequency of each of the examination regions included in the sectional views of the subject, thereby further improving the results of the examination.

Figure 9:
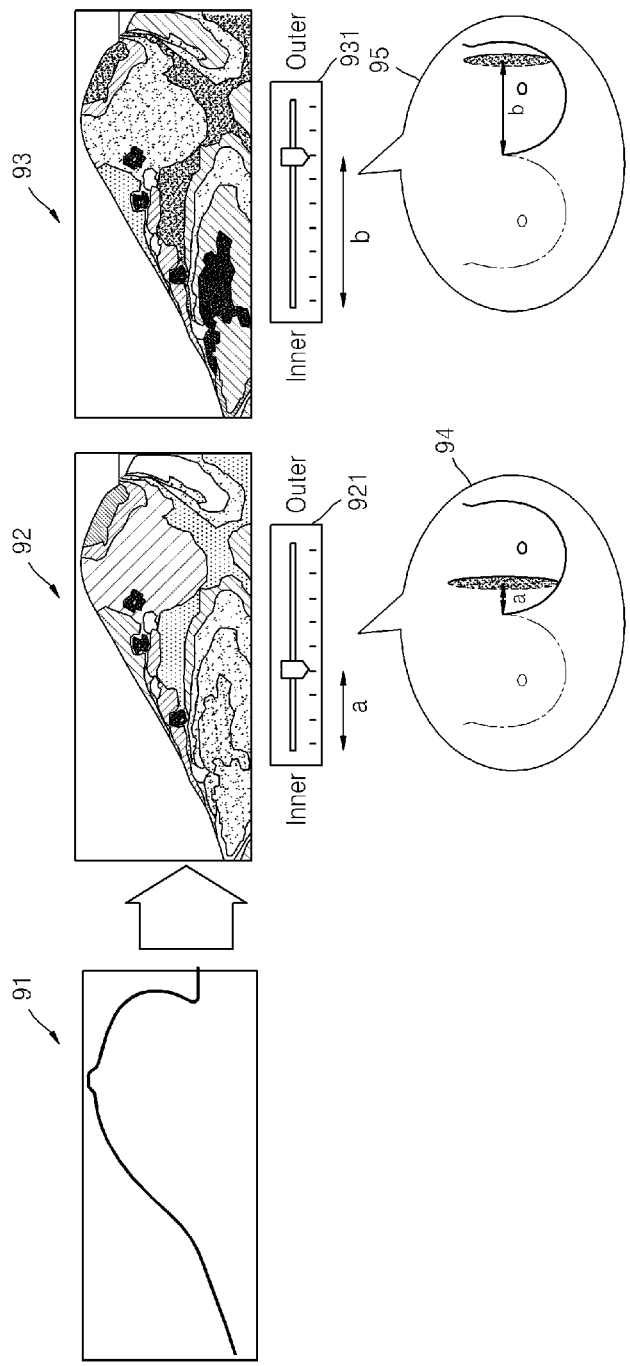
FIG. 9 is a diagram illustrating an example of a method of viewing diagnostic image indicating each of sectional views generated from a first lateral surface towards a second lateral surface of the subject or from the second lateral surface towards the first lateral surface of the subject.

FIG. 9 is a diagram illustrating an example of a method of viewing diagnostic image indicating each of sectional views generated from a first lateral surface towards a second lateral surface of the subject or from the second lateral surface towards the first lateral surface of the subject. Referring to FIGS. 3 and 9, drawing 91 indicates a lateral surface of the subject, a first diagnostic image 92 indicates the first sectional view of the subject, and a second diagnostic image 93 indicates the second sectional view of the subject. In this case, the first diagnostic image 92 and the second diagnostic image 93 further include information indicating a degree of a collision frequency of each of the examination regions included in the first sectional view and the second sectional view, respectively. The degree of the collision frequency of each of the first diagnostic image 92 and the second diagnostic image 93 is illustrated as a spectrum, as described with reference to FIG. 2.

The user may view the diagnostic images for each respective sectional view generated from the first lateral surface towards the second lateral surface or from the second lateral surface towards the first lateral surface by manipulating the user interface unit 170. In this case, the user interface unit 170 may be implemented as slider bars 921 and 931.

As a non-limiting example, in response to the subject being a breast, the first lateral surface of the subject is a portion around the cleavage, and the second lateral surface of the subject is an external portion around the armpit, or vice versa.

For example, in response to the slider bar 921 being manipulated by the user, the first sectional view indicated by the first diagnostic image 92 indicates a first sectional view generated so as to be spaced apart from the first lateral surface by distance 'a', as shown in drawing 94.

In addition, in response to the slider bar 931 being manipulated by the user, the second sectional view indicated by the second diagnostic image 93 indicates a second sectional view generated so as to be spaced apart from the first lateral surface by a distance 'b', as shown in drawing 95.

Similarly, the user may view the diagnostic images indicating sectional views in desired positions by manipulating the user interface unit 170 implemented as the slider bar 921 and 931. In this case, the diagnostic image further includes the information indicating the degree of the collision frequency of each of the examination regions included in the sectional views of the subject, thereby further improving the results of the examination.

Figure 10:
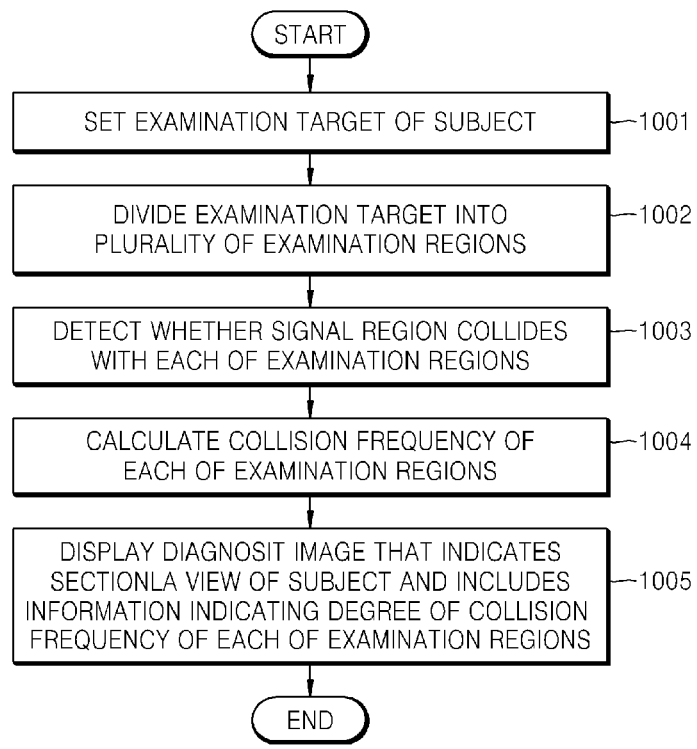
FIG. 10 is a flowchart illustrating an example of a method of displaying a diagnostic image.

FIG. 10 is a flowchart illustrating an example of a method of displaying a diagnostic image. Referring to FIG. 10, the method of displaying the diagnostic image includes time-series operations performed by the image processing device 100 and the medical image system 300 illustrated in FIGS. 1 and 3. Thus, it is understood as being within the scope of the teachings herein that the above descriptions for the image processing device 100 and the medical image system 300 illustrated in FIGS. 1 and 3 are also applicable to the method of displaying of the diagnostic image illustrated in FIG. 10.

In operation 1001, the examination target setting unit 110 sets an examination target of a subject. In this case, the examination target is a portion of the subject to be examined. The examination target may be set based on information that is previously stored, or may be set by using a probe.

In operation 1002, the examination target dividing unit 120 divides the examination target set in operation 1001 into a plurality of examination regions. In this case, as a non-limiting example, the examination target may be divided into the examination regions that are each shaped like a unit hexahedron with a predetermined size. The predetermined size may be changed by the user.

In operation 1003, the detector 130 detects whether a signal region indicated by a signal from a probe collides with each of the examination regions divided in operation 1002. In this case, as a non-limiting example, the probe may be the ultrasonic probe 50.

In operation 1004, the calculator 140 calculates a collision frequency of each of the examination regions, based on the detection result of operation 1003.

In operation 1005, the user interface unit 170 displays a diagnostic image that indicates a sectional view of the subject and indicates information indicating the degree of the collision frequency of each of the examination regions included in the sectional view of the diagnostic image, based on the calculation result of operation 1004. As another aspect, without the user interface unit 170 for displaying the diagnostic image, the display unit 210 may display the diagnostic image.

Thus, the user may recognize examination regions on which the examination is not performed or is not perfectly performed, with reference to the information indicating the collision frequency of each of the examination regions included in the sectional view of the subject, thereby improving the results of the examination.

An example of a medical device including an image processing device includes an endoscope.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of displaying a diagnostic image, the method comprising:
    setting an examination target of a subject;
    dividing the examination target into a plurality of examination regions;
    detecting whether a signal region indicated by a signal transmitted from a probe collides with each of the plurality of examination regions;
    calculating a collision frequency of each of the plurality of examination regions based on a result of the detecting; and
    displaying a diagnostic image that indicates a sectional view of the subject and includes information indicating the collision frequency of each of the plurality of examination regions included in the sectional view based on the calculation result
    wherein the collision frequency is calculated by increasing a value of the collision frequency whenever a collision occurs, and
    wherein the collision indicates that predetermined portions of the signal region and each of the plurality of examination regions contact each other for a predetermined period of time.

2. The method of claim 1, wherein the displaying comprises displaying a second diagnostic image by changing a first diagnostic image indicating a first sectional view of the subject to the second diagnostic image indicating a second sectional view which corresponds to a different sectional plane of the examination target than the first sectional view, according to manipulation,
    wherein the second diagnostic image further includes information indicating the collision frequency of each examination region included in the second sectional view of the subject.

3. The method of claim 1, wherein the displaying comprises displaying the diagnostic image indicating each of sectional views generated from a front surface towards a rear surface of the subject or from the rear surface towards the front surface of the subject, according to manipulation,
wherein the diagnostic image further includes information indicating the collision frequency of each examination region included in a sectional view indicated by the diagnostic image.

4. The method of claim 1, wherein the displaying comprises displaying the diagnostic image indicating sectional views generated from a first lateral surface towards a second lateral surface of the subject, according to manipulation,
wherein the second lateral surface is positioned in an imaginary straight line passing through the subject with the first lateral surface; and
the diagnostic image further includes information indicating the collision frequency of each examination region included in a sectional view indicated by the diagnostic image.

5. The method of claim 2, further comprising manipulating a user interface unit implemented as a slider bar so as to display the diagnostic image indicating a sectional view of a desired position of the subject.

6. The method of claim 1, further comprising determining examination regions by setting zero as a collision frequency of examination regions of a non-subject region from among the plurality of examination regions.

7. The method of claim 6, wherein the determining of the examination regions comprises determining the examination regions by using a switch or pressure sensor included in the probe or by using information indicating whether an image obtained from a signal received from the probe is an empty image.

8. The method of claim 1, wherein the setting of the examination target comprises setting the examination target by recognizing a plurality of points indicating an outer appearance of the subject by using a sensor included in the probe.

9. The method of claim 1, further comprising providing information indicating that the examination regions of the diagnostic image contains an examination region having a collision frequency that is equal to or less than a threshold value to the user.

10. A non-transitory computer-readable recording medium having stored thereon a program for executing the method of claim 1.

11. The method of claim 1, wherein
the calculated collision frequency comprises a plurality of collisions per examination region for one or more of the plurality of examination regions; and
the displaying comprises displaying the examination target comprising different colors or color intensities based on the collision frequencies of the one or more examination regions which include a plurality of collisions.

12. The method of claim 1, wherein the display distinguishes an examination region where the collision frequency is below a predetermined threshold from an examination region where the collision is above the predetermined threshold.

13. An image processing device comprising:
an examination target setting unit configured to set an examination target of a subject;
an examination target dividing unit configured to divide the examination target into a plurality of examination regions;
a detector configured to detect whether a signal region indicated by a signal transmitted from a probe collides with each of the plurality of examination regions;
a calculator configured to calculate a collision frequency of each of the plurality of examination regions, based on a result of the detecting; and
a diagnostic image generating unit configured to generate a diagnostic image that indicates a sectional view of the subject and includes information indicating a degree of the collision frequency of each of the plurality of examination regions included in the sectional view, based on the calculation result, wherein
the collision frequency is calculated by increasing a value of the collision frequency whenever a collision occurs;
the collision indicates that predetermined portions of the signal region and each of the plurality of examination regions contact each other for a predetermined period of time; and
the examination target setting unit, the examination target dividing unit, the detector, the calculator, and the diagnostic image generating unit are implemented by one or more processors.

14. The image processing device of claim 13, wherein the diagnostic image generating unit generates a second diagnostic image by changing a first diagnostic image indicating a first sectional view of the subject to the second diagnostic image indicating a second sectional view different from the first sectional view, according to manipulation, and
wherein the second diagnostic image further includes information indicating a degree of a collision frequency of each examination region included in the second sectional view of the subject.

15. The image processing device of claim 13, wherein the diagnostic image generating unit generates the diagnostic image indicating each of sectional views generated from a front surface towards a rear surface of the subject or from the rear surface towards the front surface of the subject, according to manipulation, and
wherein the diagnostic image further includes information indicating a degree of a collision frequency of each examination region included in a sectional view indicated by the diagnostic image.

16. The image processing device of claim 13, wherein the diagnostic image generating unit generates the diagnostic image indicating each of sectional views generated from a first lateral surface towards a second lateral surface of the subject, according to manipulation
wherein the second lateral surface is positioned in an imaginary straight line passing through the subject with the first lateral surface, and
wherein the diagnostic image further includes information indicating a degree of a collision frequency of each of examination regions included in a sectional view indicated by the diagnostic image.

17. The image processing device of claim 14, further comprising a user interface unit configured to be manipulated by a user so as to display the diagnostic image indicating a sectional view of a desired position of the subject.

18. The image processing device of claim 13, further comprising an examination region determination unit configured to determine the examination regions by setting zero as a collision frequency of examination regions of a non-subject region from among the plurality of examination regions.

19. A medical image system comprising:
an ultrasonic probe configured to transmit or receive an ultrasonic signal to or from a subject;
an image processing device configured to set an examination target of a subject, divide the examination target into a plurality of examination regions, detect whether a signal region indicated by a signal transmitted from the ultrasonic probe collides with each of a plurality of examination regions of the subject, calculate a collision frequency of each of the plurality of examination regions, based on a result of the detecting, and generate a diagnostic image that indicates a sectional view of the subject and includes information indicating a degree of the collision frequency of each of the plurality of examination regions included in the sectional view based on the calculation result; and
a display configured to display the diagnostic image, wherein
the collision frequency is calculated by increasing a value of the collision frequency whenever a collision occurs;
the collision indicates that predetermined portions of the signal region and each of the plurality of examination regions contact each other for a predetermined period of time; and
the image processing device is implemented by one or more processors.

20. The medical image system of claim 19, wherein the image processing device generates a second diagnostic image by changing a first diagnostic image indicating a first sectional view of the subject to the second diagnostic image indicating a second sectional view different from the first sectional view, according to manipulation, and
wherein the second diagnostic image further includes information indicating a degree of a collision frequency of each examination region included in the second sectional view of the subject.

21. The medical image system of claim 19, wherein the image processing device generates the diagnostic image indicating each of sectional views generated from a front surface towards a rear surface of the subject or from the rear surface towards the front surface of the subject, according to manipulation, and
wherein the diagnostic image further includes information indicating a degree of a collision frequency of each examination region included in a sectional view indicated by the diagnostic image.

22. The medical image system of claim 19, wherein the image processing device generates the diagnostic image indicating each of sectional views generated from a first lateral surface towards a second lateral surface of the subject, according to manipulation
wherein the second lateral surface is positioned in an imaginary straight line passing through the subject with the first lateral surface, and
wherein the diagnostic image further includes information indicating a degree of a collision frequency of each examination region included in a sectional view indicated by the diagnostic image.

* * * * *